United States Patent [19]

Pearlstein et al.

[11] Patent Number: 5,516,939
[45] Date of Patent: May 14, 1996

[54] STARCH AND GRAIN WITH A NOVEL GENOTYPE

[75] Inventors: Richard W. Pearlstein; James F. Ulrich, both of Newark, Del.

[73] Assignee: E. I. Du Pont de Nemours and Company, Wilmington, Del.

[21] Appl. No.: 261,564

[22] Filed: Jun. 17, 1994

[51] Int. Cl.$^6$ .......................... C08B 31/00; C08B 33/00
[52] U.S. Cl. ................................................ 536/102
[58] Field of Search ................................................ 536/102

[56] References Cited

U.S. PATENT DOCUMENTS

| | | | |
|---|---|---|---|
| 4,789,557 | 12/1988 | Friedman et al. | 426/578 |
| 4,801,470 | 1/1989 | Friedman et al. | 426/578 |
| 5,009,911 | 4/1991 | Mauro et al. | 426/578 |

OTHER PUBLICATIONS

Whister et al. (Eds) Starch: Chemistry and Technology, Academic Press, New York, 1965, pp. 14–17.
Webster's II New Riverside University Dictionary, 1988, p. 753.
Brockett, E. et al, "Gelatinization Characteristics of Starch from du, wx, ae, and ae wx, Endosperm of Sweet Corn Inbred la5125", Paper No. 7807, PA Agricultural Experimental Station Series, The Pennsylvania State University, University Park, PA.
Boyer, C. D. et al, "Interaction of the Amylose–Extender and Waxy Mutants of Maize", *The Journal of Heredity*, 67, 209–214, 1976.
Yamada, T. et al, "A Novel type of Corn Starch from a Strain of Maize", *Starch/Stärke*, 30, 145–148, 1978.

*Primary Examiner*—Nathan M. Nutter

[57] ABSTRACT

Grain, produced by a starch bearing plant, which is homozygous recessive for the waxy gene and heterozygous for the amylose extender gene and also one of the dull, sugary, or shrunken genes yields a starch with novel functional properties which can be utilized for foodstuffs and other applications without chemical modifications.

3 Claims, 2 Drawing Sheets

STARCH AND GRAIN WITH A NOVEL GENOTYPE

FIELD OF THE INVENTION

This invention relates to starch bearing plants and to starch which has been obtained from a grain or vegetative plant part with a novel genotype homozygous recessive for the waxy gene (wx), heterozygous for the amylose extender gene (ae), and heterozygous for either the dull (du), sugary-1 (su1), or shrunken-1 (sh1) genes.

BACKGROUND OF THE INVENTION

Starch is a mixture of two polysaccharides, amylose and amylopectin. Amylose is an unbranched chain of up to several thousand α-D-glucopyranose units linked by α-1-4 glycosidic bonds. Amylopectin is a highly branched molecule made of up to 50,000 α-D-glucopyranose residues linked by α-1-4 and α-1-6 glycosidic bonds. Approximately 5% of the glycosidic linkages in amylopectin are α-1-6 bonds, which leads to the branched structure of the polymer.

Amylose and amylopectin molecules are organized into granules that are stored in plastids. The starch granules produced by most plants are 15–30% amylose and 70–85% amylopectin. The ratio of amylose to amylopectin and the degree of branching of amylopectin affects the physical and functional properties of the starch. Functional properties, such as viscosity and stability of a gelatinized starch, determine the usefulness and hence the value of starches in food and industrial applications. Where a specific functional property is needed, starches obtained from various crops such as maize, rice, or potatoes may meet the functionality requirements. If a starch does not meet a required functional property, if for example it must have stable viscosity under high temperatures and acidic conditions, the functionality can sometimes be achieved by chemically modifying the starch. Various types and degrees of chemical modification are used in the starch industry, and the labelling and use of chemically modified starches must meet government regulations.

Within the starch bearing organs of plants, the proportion of amylose to amylopectin and the degree of branching of amylopectin are under genetic control. For example, plants homozygous recessive for the waxy gene lack a granule bound starch synthase enzyme and produce nearly 100% amylopectin. Plants homozygous recessive for the amylose extender gene can produce starch granules that are up to 90% amylose. The dull gene has been shown to control the activity of a starch branching enzyme.

Genes that have their primary effect on starch or protein synthesis, including amylose extender (ae), brittle (bt), dull (du), floury (fl), horny (h), opaque (o), shrunken (sh), sugary (su), and waxy (wx), are referred to as recessive genes because their effect on kernel appearance can be masked in F1 seed by the presence of a dominant form of each respective gene. Conventional nomenclature of plant varieties has been established to identify genotypes that carry a particular gene of interest. For the previously listed genes, genotypes are identified by the homozygous recessive mutant alleles they carry. Other genes not listed in the variety name are homozygous dominant. For example, a variety described as ae wx is homozygous recessive for the amylose extender and waxy genes and homozygous dominant for the other starch biosynthesis genes such as brittle, dull, shrunken, and sugary. According to conventional genetics teaching, the effect of a recessive gene is not expressed unless the gene is homozygous recessive. Hence, reports on the properties of starch from mutant plant species typically describe starch obtained from plants homozygous recessive for a particular gene or combination of genes. The properties of starch obtained from maize plants homozygous recessive for ae, du, wx, and aewx are reported in an article by E. Brockett et al. entitled "Gelatinization Characteristics of Starch from du, wx, ae, and aewx Endosperm of Sweet Corn Inbred Ia5125", published in Starch/Starke 40 (1988) Nr. 5. pp. 175–177.

In cereal grains such as maize (Zea mays L.), the kernel is the product of double fertilization (Kiesselbach, T. A., 1980, The Structure and Reproduction of Corn, University of Nebraska Press). The pollen grain contains two sperm nuclei. At the time of fertilization one of the sperm nuclei fuses with the nucleus of the ovule to form the embryo of the seed, and one fuses with two female nuclei to form the endosperm of the seed. The endosperm receives two thirds of its genetic material from the female plant and one third from the pollen. The immediate effect of pollen on the developing seed is termed xenia. The number of copies of a particular gene present in a cell, such as an endosperm cell, is known as the gene dose. Gene dosage effects have been studied for the ae and wx genes. In non-waxy maize, the ae allele is usually completely recessive to the dominant allele Ae with respect to kernel appearance. In waxy maize, kernels with varying doses of the ae allele can often be visually distinguished from each other. The effect on starch properties of various doses of ae in waxy maize has been shown by T. Yamada et al. in an article entitled "A Novel Type of Corn Starch from a Strain of Maize" published in Starke 30 (1978) Nr. 5, pp. 145–148. The interaction of various doses of ae and wx on starch accumulation and apparent amylose content was reported by Boyer et al. in The Journal of Heredity, 67:209–214 1976. No reports of the effect of various doses of du, su1, or sh1 on the properties of starch have been presented in the art.

Several U.S. patents describe the utility of various homozygous recessive gene combinations on starch production. The patents describe starch extracted from plants homozygous recessive for double or triple mutant gene combinations. For example, U.S. Pat. No. 4,789,557 relates to starch extracted from a plant homozygous recessive for the du and wx genes and U.S. Pat. No. 5,009,911 relates to starch extracted from a plant homozygous recessive for the ae and wx genes. There have been no patents describing the use of starch obtained from heterozygous grain.

Most cereal crops are handled as commodities, and many of the industrial and animal feed requirements for these crops can be met by common varieties which are widely grown and produced in volume. However, there exists at present a growing market for crops with special end-use properties which are not met by grain of standard composition. Most commonly, specialty maize is differentiated from "normal" maize, also known as field corn, by altered endosperm properties, such as an overall change in the degree of starch branching as in waxy or high amylose maize, an increased accumulation of sugars as in sweet corn, or an alteration in the degree of endosperm hardness as in food grade maize or popcorn; Glover, D. V. and E. T. Mertz, 1987, Corn. In: Nutritional Quality of Cereal Grains; Genetic and Agronomic Improvement, R. A. Olson and K. J. Frey, eds. American Society of Agronomy, Madison, Wis., pp. 183–336; Rooney, L. W. and S. O. Serna-Saldivar, 1987, Food Uses of Whole Corn and Dry-Milled Fractions, In: Corn:Chemistry and Technology, S. A. Watson and P. E. Ramstead, eds. American Association of Cereal Chemists, Inc., St. Paul, Minn., pp. 399–429. "Specialty" crops are typically grown under contract for specific end users who place value on starch quality or other specific quality attributes. A specialty crop such as waxy maize is more valuable as a raw material to the starch industry than is normal or commodity grade maize, and thus is referred to as a value added crop. Currently the market size and added value of waxy maize is such that approximately 150,000 acres are grown in the United States. Farmers are paid a premium for growing specialty crops such as waxy maize because it is more valuable than normal maize and must not be mixed with normal maize. The current invention offers the buyers of value added crops like waxy maize a source of starch having properties superior to waxy starch and offers farmers the opportunity to grow a higher value crop than normal or waxy maize.

Purified starch is obtained from plants by a milling process. Maize starch is extracted from kernels through the use of a wet milling process. Wet milling is a multi-step process involving steeping and grinding of the kernels and separation of the starch, protein, oil, and fiber fractions. A review of the maize wet milling process is given by S. R. Eckhoff in the Proceedings of the Fourth Corn Utilization Conference, Jun. 24–26, 1992, St. Louis, MO., printed by the National Corn Growers Association, CIBA-GEIGY Seed Division and the United States Department of Agriculture. Starch is used in numerous food and industrial applications and is the major source of carbohydrates in the human diet. Typically, starch is mixed with water and cooked to form a thickened gel. Three important properties of a starch are the temperature at which it cooks, the viscosity the gel reaches, and the stability of the gel viscosity over time. The physical properties of unmodified starch during heating and cooling limit its usefulness in many applications. As a result, considerable effort and cost is needed to chemically modify starch in order to overcome these limitations of starch and to expand the usefulness of starch in industrial applications.

Some limitations of unmodified starches and properties of modified starches are given in Modified Starches: Properties and Uses, O. B. Wurzburg, ed., 1986, CRC Press, Inc., Boca Raton, FL. Unmodified starches have very limited use in food products because the granules swell and rupture easily, thus forming weak bodied, undesirable gels. Depending on the food or industrial application, shortcomings of unmodified starches include excess or uncontrolled viscosity after cooking; cohesive or rubbery texture of cooked starch; structural break down during cooking or when exposed to shear or to low pH; and lack of clarity and the tendency of starch to become opaque and gel when cooled. Chemical modifications are used to stabilize starch granules thereby making the starch suitable for thousands of food and industrial applications including baby foods, powdered coffee creamer, surgical dusting powders, paper and yarn sizings, and adhesives. Common chemical modifications include cross linking in which chemical bonds are introduced to act as stabilizing bridges between starch molecules, and substitution in which substituent groups such as hydroxyethyl, hydroxypropyl or acetyl groups are introduced into the starch molecules.

Cross linking and substitution are multi-step processes involving reactions that are usually run on aqueous suspensions of starch at wide ranges of temperature and pH. Cross linking reactions are often run for 1 to 5 hours at 40° C. to 50° C. and pH 8 to 12. However, cross linking under acidic conditions and for up to 28 hours is necessary for some applications; Wurzburg, O. B., 1986, Cross-Linked Starches, In Modified Starches: Properties and Uses; O. B Wurzburg, ed.; pp. 41–53. Cross linking reinforces hydrogen bonds in starch granules with chemical bonds between molecules. When aqueous suspensions of non-cross linked starches are heated, hydrogen bonds weaken, allowing water to enter the granules, causing them to swell, fragment, rupture, and collapse. When this happens, the starch develops a cohesive, rubbery texture. Cross linking reinforces the hydrogen bonds upon heating, thus providing varying degrees of granule stability, depending on the number of cross links. Cross linked starches are used to a wide extent in foods, paper, textiles, and adhesives. Other chemical modifications, such as substitutions, very often depend on cross linking to impart a desired property.

Cross linked starches are used in foods, textiles, and adhesives, with the main use for high viscosity starches being as thickeners for food products; Jarowenko, W., 1986, Acetylated Starch and Miscellaneous Organic Esters. In Modified Starches: Properties and Uses, O. B. Wurzburg, ed., CRC Press, Boca Raton, Fla., pp. 55–77. Food starch thickeners must be stable under various conditions such as low pH, high speed mixing (shear), refrigeration, and freeze-thaw cycles. Cross linking provides resistance to low pH and shear, but the starches synerese (lose water holding capacity) during refrigeration. Therefore, cross linking is often combined with substitution to improve the thickening performance of starch. Cross-linked starches are stabilized by the addition of substituents such as acetyl, phosphoryl, and hydroxypropyl groups. The substitution reactions normally require the use of high concentrations of a salt to prevent starch granule gelatinization under the required conditions of high temperature and high pH. These cross-linked, substituted starches are used in baked, frozen, canned, and dry foods. Common uses are in pie fillings, gravies, custards, and cream fillings.

The use of chemically modified starches in the United States is regulated by the Food and Drug Administration (FDA). The Federal Food, Drug, and Cosmetic Act allows for two types of modified starches to be used in the food industry, "food starch-modified" and "industrial starch-modified". Food starch-modified may be used in food but must meet certain treatment limits, and industrial starch-modified may be used in items such as containers that come in contact with food and must also meet specified treatment requirements; Code of Federal Regulations, Title 21, Chapter 1, Part 172, Food Additives Permitted in Food for Human Consumption, Section 172, 892, Food Starch-Modified, U.S. Government Printing Office, Washington, D.C. 1981; (a) Part 178, Indirect Food Additives, Sect. 178.3520, Industrial Starch-Modified. These regulations limit the degree of chemical modification by defining the maximum amount of chemical reagent that can be used in the modification steps. The levels of by-products in starch resulting from the modification process are also regulated. For example, propylene chlorohydrin residues in hydroxypropyl starch are of special concern; Tuschhoff, J. V., 1986, Hydroxypropylated Starches, In Modified Starches: Properties and Uses, O. B. Wurzburg, ed., CRC Press, Boca Raton, FL, pp. 55–77.

The present invention offers a way to produce starch with the functional properties of certain chemically modified starches, without the need for chemical modification. Starch of the present invention can be used in food products as a direct replacement for chemically modified starch. By eliminating the chemical modification steps, the present invention offers the starch industry considerable cost and time savings, and dramatic reductions in waste treatment needs. Also, the present invention offers the starch industry a new type of starch with physical and functional properties not attainable through chemical modification. This new starch is also expected to serve as a superior base starch for chemical modifications by providing superior functionality at much lower levels of cross-linking and substitution than are currently required using a normal waxy base starch.

SUMMARY OF THE INVENTION

Applicants have discovered a novel starch with improved functional properties which is useful in a wide range of food and industrial applications without the need for chemical modification. This starch is obtained from a grain produced by a novel combination of the waxy (wx), amylose extender (ae), and either of sugary-1 (su1), dull (du), or shrunken-1(sh1) genes, produced by cross pollination of double mutant aewx plants by either su1wx, duwx, or sh1wx plants. Specifically, one aspect of the present invention is a grain produced by a starch bearing plant in which the genotype of the grain comprises a genome which is homozygous recessive for the wx gene, heterozygous for the ae gene, and heterozygous for a gene selected from the group consisting of the su1, du, and sh1 genes. Another aspect of the present invention involves a method for making a thickened foodstuff by combining an effective amount of the starch extracted from the novel grain of Applicants' invention with water and a foodstuff and cooking the resulting composition as necessary to produce a thickened foodstuff. Maize is preferred as a starch bearing plant by virtue of established breeding strategies and widespread production, two doses of the recessive ae allele are preferred due to greater improvement in functionality of starch and single dose heterozygous genotypes for du, sh and su are preferred based upon the ease of preparation.

DESCRIPTION OF THE INVENTION

The present invention teaches that grain heterozygous at the du, su1, or sh1 genes, heterozygous at the ae gene, and homozygous recessive at the wx gene will produce starch functionally superior to waxy, dull waxy, and amylose extender waxy starches, and can replace chemically modified starches. Valuable properties of this new starch are higher paste viscosity, greater shear resistance, and greater acid resistance than waxy or dull waxy (du wx) maize starch. In contrast with amylose extender waxy (ae wx) starch, this new starch offers much lower pasting temperature, and much greater stability and clarity of the cooked paste. The starch of the present invention is suitable for use in a wide range of food and industrial products in its native form, and would also be a superior base starch for chemical modification.

A major advantage of the starch of the present invention is that it can be used as a thickener without being chemically modified. In industrial or food product applications where a specific functional property is needed, starches are most commonly altered by chemical modification. By reducing or eliminating the need for chemical modification, starch manufacturers will save money and food product manufacturers will be able to offer products containing natural food starch. This natural starch could be used in countries where some chemically modified food starches are prohibited by law.

Figure 1:
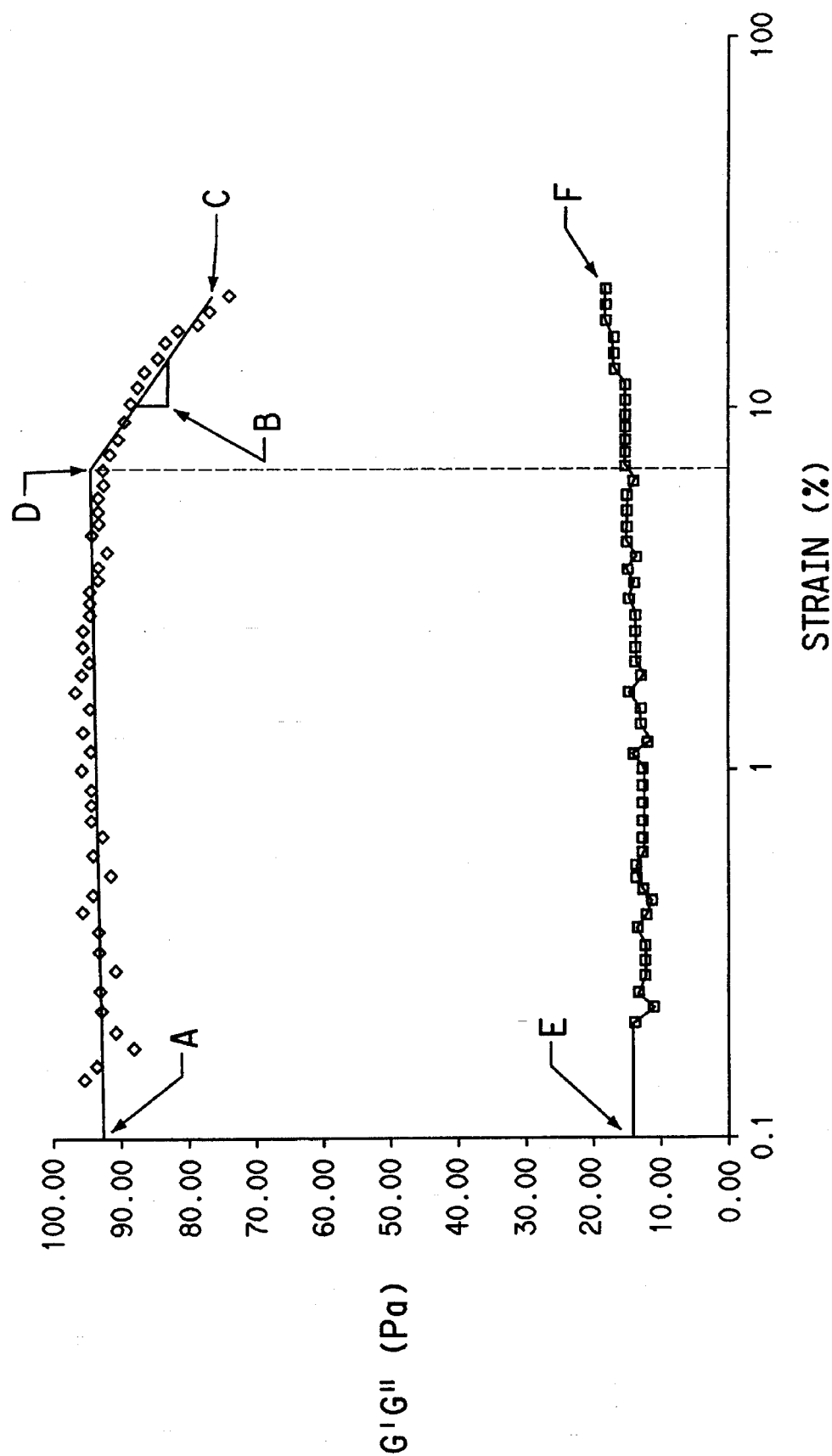
FIG. 1 shows the generalized behavior of a 5% (Dry Solids Basis) viscoelastic starch paste in which the elastic (G') and viscous (G") too dull, which are components of the viscosity of a gel, are plotted against the strain, which is a measure of the deformation of the gel In FIG. 2, 'A' shows the elastic modulus at zero strain, 'B' the plasticity, 'C' the elastic modulus at 20% strain, 'D' the yield strain, 'E' the viscous modulus at zero strain, and 'F' the viscous modulus at 20% strain.

In the context of this disclosure, a number of terms are used relevant to plant breeding and starch characterization. As used herein, the term "allele" refers to one of two or more forms of a gene that exists at a chromosome location, distinguished by their differing effects on the phenotype. "Chemically modified starch" refers to a starch that has been subjected to processes such as cross linking, derivitization, substitution, or other processes that involve chemical treatment to impart desired functional properties. A "female plant" is any plant incapable of producing or shedding viable pollen. The term "field corn" refers to the commonly grown commodity grade maize used for grain and/or forage, also known as dent corn when the kernels have an indented crown. "Gel quality" is a viscoelastic property of a gel measured by the ratio of viscous modulus to elastic modulus. If the ratio is 1 or greater, the material displays a more liquid-like than solid-like behavior (See FIG. 1). "Gel strength" is a viscoelastic property of a gel calculated from the elastic (G') and viscous (G") moduli using the following equation:

$$\text{Gel strength} = \sqrt{G'^2 + G''^2}.$$

"Genome" refers to the entire set of genetic information found within a cell of an organism, while "genotype" is the genetic constitution in respect to the alleles at one, a few, or many of the alleles under observation.

Also relevant to this disclosure is the term "grain" which is the starch bearing, reproductive organ of a plant. In maize, grain is comprised of the mature kernels produced by growers for on farm use or for sale to customers while in potato and other tubers it is the vegetative plant part. The term "heterozygous" refers to a condition in which different alleles exist at corresponding loci on homologous chromosomes, while the term "homozygous" refers to a condition in which identical alleles exist at corresponding loci on homologous chromosomes. In the instant case, the heterozygous condition refers to the existence of either one or two copies of a given allele at the locus. A "male plant" is a plant capable of shedding viable pollen. "Modulus" is the ratio of stress over strain, where stress is the applied force per unit area and strain is the change in length per unit length or change in volume per unit volume. Strain can also be referred to as shear. The elastic, or storage, modulus of a starch slurry is the component of rigidity contributed by the network of polymeric materials that make up the starch. The viscous, or loss, modulus is the component of rigidity of a starch slurry contributed by the fluid components (e.g., water molecules and non-entangled carbohydrate molecules) of the slurry. The characteristics and measurements of these parameters have been described previously; Hamann et al., Applications of Thermal Scanning Rheology to the Study of Food Gels, In: Thermal Analysis of Foods;

V. R. Harwalkar and C. Y. Ma, ed.; pp. 306–332. As used herein, a "mutant" is an organism carrying a mutant gene, while a "mutant gene" is a gene that is in any way different from other, more frequently found forms of that gene. The term "pasting" refers to an irreversible physical change in starch granules or a suspension of starch granules characterized by swelling and hydration of granules, a rapid increase in viscosity of a suspension, and the formation of a sol from the suspension. This change is also known as cooking or gelatinization. The "phenotype" refers to the observable properties of an organism, produced by the interaction of the genotype and the environment. The term "plasticity" is a measure of the quality of a gel, measured as the rate of change of the elastic modulus in the nonlinear range of strain (See FIG. 1). As used herein, "polyploid" means a cell having more than two chromosome sets, or an organism composed of such cells. In maize, the kernel endosperm is triploid, a form of polyploidy in which each cell has three chromosome sets, two from the female parent and one from the male (pollen) parent. "Recessive" is a term describing an allele that is not phenotypically expressed in the heterozygous condition. The abbreviation "SNU" refers to the stirring number unit, approximately equal to 10 centipoise, which is a measure of viscosity. For conversion to SI units (pascal seconds), multiply centipoise by 1000, i.e., 1 PaSec=1000 cp. Hence, 1 SNU=0.01 PaSec. The term "sol" refers to a fluid colloidal system. A "starch bearing plant" is a crop plant commercially grown for the harvest of grain. The "viscosity" is a measure of the internal friction of a fluid that can be thought of as the consistency or thickness of a fluid. And finally, the "yield strain" refers to the strain at which a material starts displaying nonlinear viscoelastic behavior (See FIG. 1).

To produce the heterozygous grain of the present invention, homozygous recessive ae wx plants are cross pollinated with homozygous recessive du wx, su1 wx, or sh1 wx plants. The male plants used to make the cross pollination are homozygous dominant for the ae gene.

To develop a double mutant plant homozygous recessive for the ae and wx genes, a plant carrying the recessive ae allele (Parent A) is crossbred with a plant carrying the recessive wx allele (Parent B). Progeny from this cross are grown and self pollinated, producing F2 generation seeds which carry both recessive genes. If Parent A and Parent B are homozygous recessive for ae and wx respectively, then 1/16 of the F2 progeny can be expected to be homozygous recessive for both genes. These plants are used as female plants in producing grain of the present invention. The male parent double mutants are produced by the same process, using a plant carrying recessive genes for the du, su1, or sh1 genes as Parent A in the above development method.

To facilitate cross pollination, the plants to be used as the female are rendered male sterile. This can be accomplished by physical removal of the male pollen-shedding part of the plant, by chemical treatment, or by a genetic mechanism such as cytoplasmic male sterility. In maize, the male part of the plant is the tassel which can be easily removed by hand or machine. Production of the present invention in maize requires planting male and female genotypes in close proximity in the field. Typically four rows of female plants alternate with one row of male plants when only the female plants are to be harvested for seed or grain; Female plants are rendered male sterile and are pollinated by male plants. Grain is harvested from female plants for subsequent starch extraction.

However, to facilitate mechanical planting and harvest of the grain of the present invention, the seed required to grow the male and female plants are mixed uniformly and planted together in the field. In the preferred mode, the percentage of male plants in the field will range between 5% and 20% to ensure adequate pollen without significantly altering the desired starch phenotype of the grain or significantly reducing starch yield. Since the female plants are rendered male sterile by such means as cytoplasmic male sterility, essentially all pollen in the field is produced by the male plants, thus the female plants bear only grain of the desired heterozygous phenotype. This production system requires that the female plants be separated by sufficient distance, preferably at least 200 meters, from pollen-shedding maize plants differing in genotype from the male plants. In this production system, the male plants will be self-pollinated, and the grain produced on those plants will be homozygous for the starch mutants comprising their genome. In all of the male genotypes (duwx, su1wx, sh1wx) used to produce grain of the present invention, the starch of the homozygous double mutants will be functionally inferior to the starch of the present invention, providing lower paste viscosity and less shear resistance. Also, due to their homozygous double mutant condition, the kernels on the male plants will accumulate significantly less starch in their endosperm than either normal waxy grain or grain of the present invention. The grain harvested from the male plants, mixed with the grain harvested from the female plants, will dilute the superior functionality of the starch obtained from the female plants, and will also decrease the total amount of starch obtained from the grain. Enough male plants must be present in the field to ensure adequate pollination, but excessive numbers of male plants are undesirable due to these effects. Pollen production from the male plants should occur at the same time as the silks on the female plants are receptive to pollen to obtain maximum production of the desired grain with the minimum number of male plants, and also the male plants could be bred for maximum pollen production and minimum grain production.

Starch of the present invention could be produced in potato (*Solanum tuberosum* L.) and the heterozygous genotype could be maintained indefinitely by vegetative propagation. The double mutants ae wx, du wx, su1 wx, and sh1 wx could be introduced into potato plants as follows: The mutant genes ae, du, su1, sh1, and wx, could be introduced into potato plants in several ways including mutagenesis of seeds by treatment with ionizing radiation or chemical mutagens such as ethyl methane sulfonate, or by tissue culture induced somaclonal mutation. Most potato species are diploid (i.e., two chromosome sets), however, the most commonly grown species, *S. tuberosum*, is tetraploid (i.e., four chromosome sets). Genetic studies and the production of homozygous mutants are easier in diploid species than in tetraploid species. Diploid plants can be produced from tetraploid plants by several ways including interspecific or intergeneric hybridization, irradiation, chemical treatment, or anther and pollen culture; Schultz-Schaeffer, J., 1980, Cytogenetics—Plants, Animals, Humans. p. 245. Springer-Verlag New York Inc. Pollination of tetraploid *S. tuberosum* plants by diploid *S. phureja* plants often gives rise to seeds having diploid embryos derived from the female plant; Hoopes, R. W., and R. L. Plaisted, 1987, Potato, pp. 385–437, In: Principles of Cultivar Development, Vol. 2., W. R. Fehr, ed., Macmillan Publishing Company. In diploid plants, single mutants could be identified by starch analysis or by analyzing the enzymes controlled by ae, du, su1, sh1, and wx. Once the single mutants are identified in diploid plants, the conventional plant breeding strategies described previously could be used to combine the mutant genes into plants homozygous recessive for the desired double mutants. Diploid plants homozygous for these double mutants can be cross pollinated to tetraploid plants. Diploid plants often produce unreduced gametes capable of fertilizing gametes of tetraploid plants thus resulting in tetraploid offspring. Progeny must be self pollinated to produce the necessary homozygous recessive double mutant plants. Flowers of homozygous ae wx tetraploid plants can be emasculated (anthers removed) and pollinated by homozygous du wx, su1 wx, or sh1 wx tetraploid plants, or vice versa, to produce heterozygous plants in accordance with the present invention. The heterozygous plants can then be vegetatively propagated to produce tubers from which starch can be extracted.

EXAMPLES

The present invention is further defined in the following examples. It will be understood that the examples are given for illustration only and the present invention is not limited to uses described in the examples. The present invention can be used for any purpose where its properties are useful such as in, but not limited to, foods, paper, plastics, adhesives, or paint. From the above discussion and the following examples, one skilled in the art of plant breeding can ascertain, and without departing from the spirit and scope thereof, can make various changes and modifications of the invention to adapt it to various usages and conditions. All such modifications are intended to fall within the scope of the intended claims. In the following examples, the symbol "*" is used to indicate the pedigree of the endosperm resulting from a cross, with the female plant indicated to the left and the male plant to the right of the *.

EXAMPLE 1a

Methodology for Production of Grain Heterozygous for the Amylose Extender Gene, Homozygous Recessive for the Waxy Gene, and Heterozygous for the Dull, Sugary, or Shrunken Genes This example illustrates the production of maize grain possessing starch of the present invention. Seed of the double mutant ae wx version of the maize line S3-61 from Pennsylvania State University was planted in the field and used as the female parent. At anthesis the silks on these plants were pollinated with pollen from one of the following double mutants: IA5125 suwx, W64A duwx (both from Pennsylvania State University) or a sh1wx line from the Maize Genetics Cooperation Stock Center (S-116 Turner Hall, Agronomy Department, University of Illinois, 1102 S. Goodwin Avenue, Urbana, Ill. 61801, USA). The triploid endosperm genotypes of these 3 types of maize grain contain 3 doses of the mutant wx gene, 2 doses of the mutant ae gene, and one mutant dose, respectively, of either the su1, du, or sh1 genes. Seed of the maize lines S3-61 aewx, W64A duwx, and IA5125 suwx have been deposited in the American Type Culture Collection (ATCC), a Budapest Treaty designated depository, Rockville, Md. 20852-1776 on Apr. 19, 1994 and have been assigned numbers 75743, 75742, and 75744, respectively.

EXAMPLE 1b

Starch Extraction

Starch was extracted from dry, mature kernels that were produced as described in Example 1a. For each sample, 15.0 grams of undamaged kernels were weighed into a 50 mL Erlenmeyer flask. Forty mL steep solution, (1% lactic acid +0.3% sodium metabisulfite in water (w/v) pH 3.82 with NaOH) was added. The tightly-stoppered flasks were held at 52° C. for 18–24 hours, then the kernels were drained and rinsed with water. The pericarps and germs were removed from each kernel with a sharpened spatula. A filtration apparatus was prepared by stretching a 72 micron mesh screen over a 15 cm plastic funnel using a rubber band then placing the stem of the funnel into a 1 liter beaker. The degerminated kernels were placed into a 120 mL square glass bottle and about 50 mL of 50 mM NaCl was added. Using a 20 mm Polytron probe (Kinematica GmbH: Kriens-Luzern, Switzerland) the kernels were alternately ground and filtered through the mesh until microscopic examination of the residue on the mesh showed no intact starch-bearing cells. The speed and duration of grinding were increased until this occurred, starting with 30 seconds at half speed and increasing to 90 seconds at full speed. Usually 4–5 grinds were needed, and about 30 g of ice was added for the full-speed grinds to prevent overheating. The combined filtrate in the beaker was brought to 400 mL with 50 mM NaCl and an equal volume of toluene was added. The mixture was stirred with a magnetic stir-bar for 1 hour at sufficient speed to completely emulsify the 2 phases. The beaker was covered with aluminum foil and the phases allowed to separate overnight. The upper toluene layer was aspirated from the beaker. The starch slurry remaining in the bottom of the beaker was resuspended, poured into a 250 mL centrifuge bottle, and centrifuged 15 minutes at 25,000 RCF. After discarding the supernatant, the starch was washed sequentially with water and acetone by shaking and centrifuging as before. The acetone was decanted and the starch allowed to dry overnight in a fume hood at room temperature.

EXAMPLE 1c

Starch Rheology

A Rapid Visco Analyzer (Newport Scientific: Sydney, Australia) with high sensitivity option and ThermoCline software was used for pasting curve analysis using the following temperature profile: Idle temperature 50° C., hold 0.5 minutes at 50° C., linear heating to 95° C. over 4 minutes, hold at 95° C. for 2.5 minutes, linear cooling to 50° C. over 4 minutes, hold at 50° C. for 4 minutes. For analysis of each starch sample, 1.50 grams of starch was weighed into the sample cup, and 25 mL of a phosphate/citrate buffer at pH 6.50 containing 1% NaCl was added.

Figure 2:
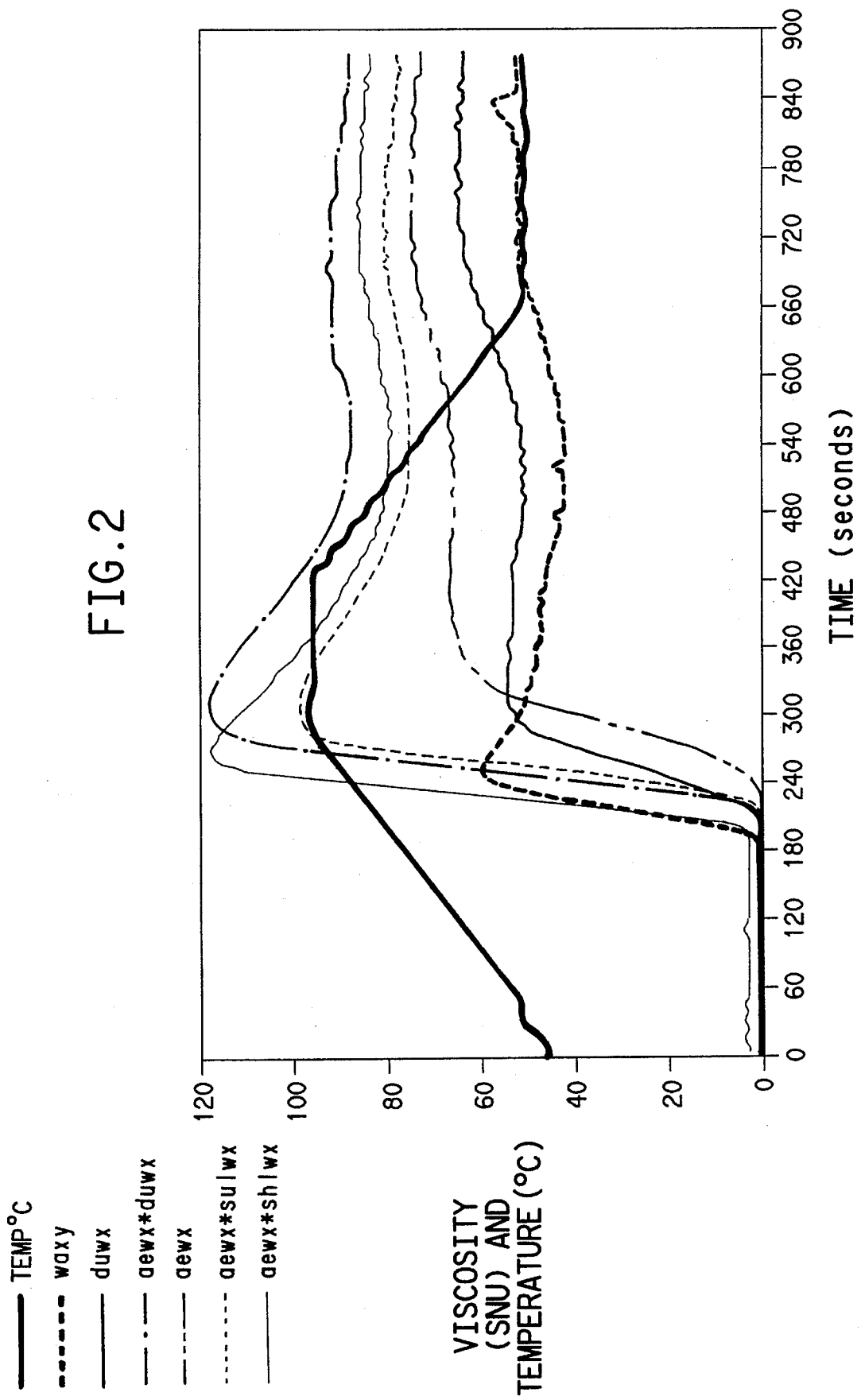
FIG. 2 shows the pasting curves for the starches extracted from the heterozygous maize endosperm genotypes of the present invention contrasted with normal waxy starch and starches extracted from the homozygous maize endosperm double mutants dull waxy and amylose extender waxy. Viscosity in stirring number units (SNU) and paste temperature in degrees Celsius have been plotted as a function of time in minutes.

Results of the Rapid Visco Analyzer pasting curves are summarized in FIG. 2. All three starches of the present invention reached hot paste viscosities and final viscosities much higher than either wx or duwx starch, and were fully gelatinized at 95° C. unlike the aewx starch.

Two rheology tests, strain sweep and viscometry, were conducted to further explore the unique properties of a starch of the present invention and compare it with wx, duwx, and aewx starches. The tests were conducted with starch paste samples (5% dry solids basis) that were cooked in an RVA for 15 minutes at the time-temperature profile described above. After cooking and prior to rheology testing, samples were held for one hour in a 25° C. water bath. Strain sweep and viscometry tests were conducted at 25° C. with a Bohlin VOR rheometer (Bohlin Instruments, Cranbury, N.J.) using a C14 couette geometry. Bohlin software, BRS4.1, was used to collect and manipulate data, and the Jobstream option in the software was used to perform the strain sweep and viscometry tests. The sample was loaded in the C14 cup so that at least 1 mm thick layer stayed above the bob. To prevent moisture loss from the sample, a solvent trap (Bohlin Instruments) was used. To eliminate the effect of loading, the sample was then sheared for 30 seconds at a low shear rate (18 $^{s-1}$). Then a programmed delay time (at least 5 minutes) was used to let the sample recover and the strain sweep test was performed. After the strain sweep test, and following another delay time, the viscometry test was performed on the same sample. The same experimental parameters and conditions were used for all samples tested.

The strain sweep test is a dynamic sinusoidal oscillation test that was conducted a 1 Hz frequency applying strain over the range 0.02% to 20%. The output from the test contains elastic and viscous moduli, phase lag, and dynamic viscosity at each of the various strains.

Plasticity, yield strain, gel quality, and gel strength were calculated from the strain sweep data (Table 1). RVA and rheological analyses demonstrate that aewx*su1wx starch has substantially different rheological properties than waxy or the double mutant duwx or aewx starches. The aewx*su1wx starch granules swelled much faster and pasted at a much lower temperature than aewx starch, resulting in much higher hot paste viscosity. Compared with wx and duwx starch, aewx*su1wx pasted at a slightly higher temperature but reached and maintained higher viscosity, like a chemically modified starch. Plasticity of the starch of the present invention was intermediate between aewx and the other two samples. The no strain gel quality showed the most solid-like behavior for aewx starch, however under 20% shear that sample was more liquid-like than any of the others, showing that the gel was not resistant to shear. The gel from the starch of the present invention was the most solid-like of all the samples at 20% strain. Gel strength followed the same trend; the waxy and dull waxy samples showed fairly low gel strength which was fairly stable under 20% strain. The aewx starch however, showed extremely high gel strength under no strain, but lost most of this strength under 20% strain. In contrast, the gel from the starch of the present invention (aewx*su1wx) showed moderately high gel strength at both no strain and 20% strain, showing excellent shear resistance.

Fillings for two pies were made, differing only in the starch used. The two starches used were WAXY-1 (product of A.E Staley Manufacturing Co., Decatur, Ill.) and a starch of the present invention extracted as in Example 1 from maize ears homozygous recessive for waxy and heterozygous for ae and su1, which were produced by pollinating aewx ears with pollen from suwx maize plants.

TABLE 2

Ingredients used to make pie filling of Example 2

| Ingredient | % | grams |
| --- | --- | --- |
| Half-and-Half | 66.67 | 400.0 |
| Sugar | 16.67 | 100.0 |
| Chocolate, unsweetened (Nestle Food Co.) | 9.33 | 56.0 |
| Starch | 5.00 | 30.0 |
| Maltrin M150 maltodextrin (GPC) | 1.50 | 9.0 |
| Vanilla extract (1X) | 0.83 | 5.0 |
| Total | 100.00 | 600.0 |

Pie fillings were made by combining ingredients listed in Table 2 in a stainless-steel double boiler, then heating while stirring at 60 RPM. After peak viscosity was attained, the fillings were held at 88° C. while stirring for 3 minutes, cooled to 4° C. and poured into pre-baked crusts for visual evaluation. Samples were stored 24 hours at 4° C., then brought to 25° C. for strain sweep and viscometry testing. Experimental methods of the strain sweep and viscometry tests are provided in Example 1c, and results of the rheological properties of the chocolate pie fillings are shown in Table 3. The gel quality of the pie filling made with WAXY-1 starch was much more liquid-like than the pie filling made with a starch of the instant invention. The gel strength of the pie filling made with a starch of the instant invention was several-fold greater than the gel strength of the pie filling made with WAXY-1 starch, both under no strain and under 20% strain. These rheological parameters demonstrating the dramatic superiority of the pie filling thickened by a starch of the instant invention establishes the correlation between the rheological properties of the starch alone and the pie filling application. These results clearly show the dramatic superiority of the starch of the instant invention over native waxy starch; providing results comparable to those obtained using chemically-modified starches.

TABLE 1

Rheological properties of aewx*sulwx starch (a starch of the present invention) compared with waxy (wx), dull waxy (duwx), and amylose extender waxy (aewx) starches

| Starch Type | Plasticity (Pa) | Gel Quality (No Strain) | Gel Quality (20% Strain) | Gel Strength (Pa) (No Strain) | Gel Strength (Pa) (20% Strain) | Yield Strain |
| --- | --- | --- | --- | --- | --- | --- |
| wx | 0.0403 | 0.5459 | 0.5781 | 6.7313 | 6.4 | 0.0685 |
| duwx | 0.0497 | 0.4776 | 0.5342 | 7.8145 | 7.3 | 0.0567 |
| aewx | 0.7026 | 0.0920 | 1.0833 | 61.7874 | 24.0 | 0.0592 |
| aewx*sulwx | 0.0940 | 0.3296 | 0.4364 | 25.3513 | 22.0 | 0.0463 |

EXAMPLE 2

Production of a Thickened Foodstuff Containing Starch of the Present Invention

This example demonstrates a utility for the starch obtained from a plant which is homozygous recessive for the wx gene and heterozygous for the ae and su1 genes. This starch serves to thicken a chocolate cream pie filling, providing functionality greatly superior to waxy starch.

TABLE 3

| | Rheological properties of chocolate pie fillings using waxy-1 starch and a starch of the present invention (aewx*sulwx) | | | | | |
|---|---|---|---|---|---|---|
| Starch Used | Plasticity (Pa) | Gel Quality (No Strain) | Gel Quality (20% Strain) | Gel Strength (Pa) (No Strain) | Gel Strength (Pa) (20% Strain) | Yield Strain |
| wx | 0.3871 | 0.5742 | 1.1250 | 55.195 | 24.0 | 0.0272 |
| aewx*sulwx | 0.4217 | 0.2586 | 0.6857 | 384.252 | 140.0 | 0.0196 |

Visual examination showed the pie made with unmodified WAXY-1 starch at the 5% level to be totally unacceptable; much too runny to allow slicing of the pie both immediately after pouring and cooling, and after refrigerated storage for 1 and 4 days. In contrast, the pie made with the starch of the present invention at the 5% level was firmly set and cuttable at all three time points, without the undesirable gel formation characteristic of unmodified dent starches. This comparison showed the vast superiority of the starch of the present invention over the other native starches, proving its suitability for replacement of chemically modified starches in a food product formula. Since the starch of the present invention combines very high paste viscosity with good stability, paste clarity, and bland flavor characteristics, it is extremely versatile and would be useful in a wide variety of food products including, but not limited to, gravies, sauces, pie fillings and puddings.

Details of the preferred embodiments of the present invention have been disclosed for illustration and should not be understood to limit either the spirit of the invention or the scope of the claims. The following claims are intended to cover all modifications of the preferred embodiments of the invention.

What is claimed is:

1. A starch extracted from a grain produced by a starch bearing plant in which the genotype of said grain comprises a genome which is homozygous recessive for the waxy gene; heterozygous with two copies of the amylose extender gene; and either heterozygous for the dull gene or heterozygous for one copy of the sugary-1 or shrunken-1 gene; and wherein said starch has a final viscosity of at leat 75 SNU.

2. A method of using a starch of claim 1 to obtain a sol comprising forming a slurry with water and an effective amount of said starch, cooking the slurry as necessary to produce said sol.

3. A method of using grain of a starch bearing plant in which the genotype of said grain comprises a genome which is homozygous recessive for the waxy gene; heterozygous with two copies of the amylose extender gene; and either heterozygous for the dull gene or heterozygous for one copy of the sugary-1 or shrunken-1 gene to obtain a starch of claim 1 comprising milling said grain.

* * * * *